United States Patent
Hufschmied

(10) Patent No.: US 9,693,840 B2
(45) Date of Patent: Jul. 4, 2017

(54) MILLING METHOD FOR THE MANUFACTURE OF DENTAL PROSTHESES

(71) Applicant: Hufschmied Zerspanungssysteme GmbH, Bobingen (DE)

(72) Inventor: Ralf Hufschmied, Bobingen (DE)

(73) Assignee: Hufschmied Zerspanungssysteme GmbH, Bobingen (DE)

( * ) Notice: Subject to any disclaimer, the term of this patent is extended or adjusted under 35 U.S.C. 154(b) by 176 days.

(21) Appl. No.: 14/398,796

(22) PCT Filed: Apr. 18, 2013

(86) PCT No.: PCT/EP2013/001153
§ 371 (c)(1),
(2) Date: Nov. 4, 2014

(87) PCT Pub. No.: WO2013/164068
PCT Pub. Date: Nov. 7, 2013

(65) Prior Publication Data
US 2015/0097305 A1    Apr. 9, 2015

(30) Foreign Application Priority Data
May 4, 2012   (DE) .......................... 10 2012 009 038

(51) Int. Cl.
*B23C 5/10* (2006.01)
*A61C 13/00* (2006.01)
*A61C 3/02* (2006.01)

(52) U.S. Cl.
CPC ............ *A61C 13/0004* (2013.01); *A61C 3/02* (2013.01); *A61C 13/0006* (2013.01);
(Continued)

(58) Field of Classification Search
CPC .......... A61C 13/0006; Y10T 29/49567; B23C 5/1018; B23C 5/1009; B23C 2210/202; B23C 2210/40; B23C 2210/203
See application file for complete search history.

(56) References Cited

U.S. PATENT DOCUMENTS 5,685,671 A    11/1997 Packer et al.

FOREIGN PATENT DOCUMENTS

EP    1 810 637 A1    7/2007
EP    2 404 689 A1    1/2012
(Continued)

OTHER PUBLICATIONS

Datron Werkzeugkatalog, Datron Tools Catalogue. p. 14 and 70.
Brasseler SGFA Flyer.
Tizian Mill, Schutz Dental Group Catalogue.

*Primary Examiner* — Jermie Cozart
(74) *Attorney, Agent, or Firm* — Varnum, Riddering, Schmidt & Howlett LLP

(57) ABSTRACT

A dental milling tool and corresponding method is provided. The dental milling tool includes a ball head portion which is rounded in a semispherical manner and which, at its largest outer diameter, approximately 1-4 mm, transitions into an axial cutting portion that runs in the axial direction with said diameter at the outer circumference in a constant manner, the axial cutting portion being adjoined by a shaft portion which extends axially with a larger or at least equally large shaft diameter. A milling method for producing dental prosthesis parts is provided wherein a dental prosthesis white body which is to be sintered into the completed dental prosthesis part is milled out of a pre-sintered ceramic white body, in particular a zirconium dioxide white body, on a multi-axis CNC milling machine with a milling tool according to one of the preceding claims using 3D freeform milling process along generated travel paths.

18 Claims, 2 Drawing Sheets

(52) U.S. Cl.
CPC .... *B23C 5/1009* (2013.01); *B23C 2210/0485* (2013.01); *B23C 2210/202* (2013.01); *B23C 2226/18* (2013.01); *F04C 2270/041* (2013.01); *Y10T 29/49567* (2015.01); *Y10T 409/303752* (2015.01)

(56) References Cited

FOREIGN PATENT DOCUMENTS

| | | | | |
|---|---|---|---|---|
| JP | WO 2011030854 A1 * | 3/2011 | ........... | B23C 5/1009 |
| JP | WO 2011149062 A1 * | 12/2011 | ............... | B23C 5/10 |
| WO | 2004/086999 A1 | 10/2004 | | |

* cited by examiner

MILLING METHOD FOR THE MANUFACTURE OF DENTAL PROSTHESES

CROSS-REFERENCE TO RELATED APPLICATIONS

This application is the U.S. national stage of PCT/EP2013/001153 filed Apr. 18, 2013, which claims priority of German Patent Application 10 2012 009 038.2 filed May 4, 2012.

TECHNICAL FIELD

The invention relates to a milling method for the manufacture of dental prostheses.

BACKGROUND DISCUSSION

Known dental milling tools or dental milling cutters have a ball end portion with curved portions of blades or cutting edges and an adjoining axial cutting portion with helical portions of blades or cutting edges and are, in their diameter, adjusted to tooth replacement parts or dental prostheses to be worked out of pre-sintered ceramic blanks or white bodies, especially zirconium oxide white bodies. That is, the diameter of the ball end, with which the dental implant or the like is to be generated, is chosen such that the tooth geometry, being provided with three-dimensional curved surfaces and notches, and not following a simple basic form, can be created with the required surface smoothness. However, for reasons of strength, the diameter can not be selected too small. A dental nose end mill intended for the processing of unfired high performance ceramics such as zirconium oxide and alumina oxide, can be found for example in the catalog 2009, S. 70 of the company Datron AG under the name "DATRON-VHM-Zirkonoxid-Dentalfräser".

For the preparation of dental prostheses such as dental implants, ceramics are employed, which are able to be sintered, due to good hygienic properties and strength values, nowadays zirconia all-ceramic materials. Therein, an unsintered ceramic blank, a so-called green body, is pre-sintered to a certain rigid hardness, ie to a so-called white body (or pre-sintered body), on which a processing with dental burs or milling tools is still easily possible, but the shrinkage occurring during sintering up to the hardness of the white body is completed before the final shaping. A dental implant white body is then sintered out, which has to be fully-sintered or sintered through, but which is already in the shape of the final dental implant. In addition to dental implants, in the same way, bridges and other dental prostheses or dental restorations are made, in particular the supporting frameworks for crowns composed of zirconium oxide, more specifically zirconia all-ceramics, which contain, in addition to the present polycrystalline zirconium oxides further stabilizing oxides such as yttrium or magnesium, e.g. 3Y-TZP, YSZ or TZ-3Y. After shaping by freeform milling on the pre-sintered white body, the resulting pre-sintered prosthesis preparation or the resulting dental prosthesis white body is then finish sintered or fully sintered, wherein the occurring sintering shrinkage or the shrinkage in volume (often approx. 50%) must be considered in the pre-shaping milling process, as the dense sintered material can not be machined or only within narrow limits, without that the structure of the ceramic takes damage.

For milling machining of the dental prosthesis white bodies, manual processing methods such as manual copy milling are known.

Here, a plastic or plaster model of the dentition is made first in the dental laboratory, e.g. from a dental impression taken by a dentist. To disconnect excessive material during the completion of such models consisting of relatively soft, but often adhering material, hand-held pneumatic turbine grinders are available to the dental technician. In most cases milling tools with bud-shaped, often with staggered toothing, right-hand or left-hand twisted or spinned (with right-hand or left-hand helix) and relatively large grinding heads in the order of a tooth are used, having broad and deep gashes to prevent clogging. The grinding head is brazed to a substantially thinner shaft or shank, so that it can be cut over the entire circumference. Such a tool can be seen for instance in the product information "Hartmetallfräser SGFA, 2007" of the company Brasseler GmbH & Co. KG.

After that, the model can then be scanned and in parallel to that, the relevant dental prosthesis white body can be milled out of the pre-sintered zirconium oxide round or plate-shaped blank. Therein, dental milling tool and scanners are clamped in parallel to one another on a corresponding copy milling machine, e.g. Titian Mill of Schütz GmbH, wherein undercuts on the prosthesis white body can be produced by a pivoting of the worktop, but, for rough and fine processing, tool changes and various fixtures of the worktop are needed.

Also in the dental field, more and more CNC milling prevails, wherein travel paths are generated using CAD/CAM-data, on which can be traveled along on multi-axis CNC milling machines by the machine in three dimensions, wherein modern CNC milling machines in addition to the three motion axes usually also have two further pivot axes, so that undercuts can be formed. The CAD/CAM-data is extracted from the scanned model or the denture scanned for instance by the dentist, so that one can speak of a computerized copy milling here, wherein the model building can be saved and also in milling even less is to do manually.

For instance, it is known from German Patent DE 696 25 012 T2, to cut out dental molds by means of CAD/CAM-generated travel paths from a suitable substrate and to insert between pairs of these moldings a polymerizable acrylate, in order to form an artificial tooth with different layers, such as a dental enamel layer, a shade layer and a backing layer. As a substrate for the forms, e.g. ceramic is proposed. The artificial tooth itself is not milled out of the substrate, but formed between tooth moldings of polymerizable acrylate.

Other automated 3D-shape milling processes or free form milling processes serve for the direct manufacturing of dental ceramics (white sintered) by milling of the dental prosthesis from pre-sintered ceramic white bodies, wherein, subsequently, the dental prosthesis is through-sintered or fully-sintered. Such a milling method is disclosed in WO2004/086999A1, for instance.

For this purpose, usually end mills having a hemispherical rounded ball end and one to four right twisted flutes are used, which have correspondingly one to four cutting edges on the outer edges of the cutting edges arranged between the flutes. For the elaboration of the dental prosthesis white body, the cutter is conveniently set from above onto the solid or full material of the respective pre-sintered ceramic round blank, and then it is step by step proceeded into the solid.

However, flaking, spalling or ruptures relatively often occurred on the partially sintered and thus relatively brittle ceramic. For the dental technician, these ruptures on the white body are at the same time the change criterion for the tool, because it can not be determined with certainty whether the tool has become dull or flaking results from the force applied on the ceramic by the milling.

Although from the processing of relatively soft materials such as plastic, wood, or as above mentioned, of gypsum, also left-hand twisted milling tools are known, which would have the advantage that during milling, no tensile force would not act on the workpiece, wherein in the machining of ceramics in particular tensile forces cause flaking, as ceramics from the above mentioned type have a relatively low tensile strength even in the white-sintered or pre-sintered state. An example of a left twisted milling tool for processing plastic, aluminum, brass or copper is provided, for example, in the 2009 catalog, page 14 of the company Datron AG under the name "DATRON VHM-Einschneider, Linksspiral rechtsschneidend". The milling tool is embodied as a single flute or single-edged tool in order for providing the large width and depth of the flute, which are usual for the machining of these materials. However, such tools can be used only if the chip discharge in downwards direction is possible. That is, not in processing cases such as 3D free-form milling, in which the milling tool is set onto the top of the solid material, but only in processing cases, in which a workpiece is machined on its vertical outer sides and the chips can be discharged downwards. Indeed, by the left-hand twist of the flutes, machining is advantageously carried out without tensile force. Thereby, the chips would be pressed downwards and would therefore lead to clogging of the tool, if chip discharge or removal is not possible in the downwards direction.

SUMMARY OF THE INVENTION

From this starting point, it is an object of the present invention to develop a milling process of the generic type in such a way that it results in increased tool life and greater process stability during milling.

This object is achieved with the features of claim 1.

The inventive milling method is characterized in that the milling is done with a left-hand twisted dental milling tool, with a plate-shaped ceramic white body is clamped and then the dental milling tool is driven from above onto and then into the solid material of the plate-shaped ceramic white body, and subsequently the milling of the dental prosthesis white body out of the plate-shaped ceramic white body is done by removing of material layer by layer along the CAD/CAM-generated travel paths. The dental milling tool used according to the invention comprises a left-hand twisted spiral geometry or a spiral geometry with a left-hand twist, which means that, extending from the ball end portion along its axial cutting portion, three or preferably two flutes and cutting teeth or splines are coiled around the web or core of the milling tool with a left-hand twist, i.e. against the direction of rotation, especially with a left-hand twist of 1° to 45° or preferably 5° to 30° to the milling tool's axis.

This is based on the surprising finding, that in particular the sinter ceramics used in dentistry allow a milling with left-hand twist also in the cases, when the chip removal in downward direction is not guaranteed. These ceramics, e.g. in the form of zirconia white bodies, are by milling pulverulently chipped and therefore do not clog a drilled or milled hole even then, when driving a left twisted dental milling tool from above into the solid material, as is the case with the milling of dental prosthesis white bodies from pre-sintered ceramic discs or round blanks. A chip congestion or chips stuck in the flutes does not occur. It is much to the positive side effect that the clamping of the white body round blanks needs to take only fewer forces than hitherto, as no tensile forces occur, which would lift up the round blank or plateshaped, but pressure forces. Until now frequently used, but relatively expensive vacuum clamping by suction of the round or plate-shaped blank can be replaced by simpler setups.

By left-hand twist, no tensile forces are applied by the cutting edges to the white body to be treated, but only compressive forces. The frequent spalling on the white body and the frequent tool change before reaching the wear limit must therefore no longer be tolerated. Since sinterable dental ceramics as zirconium oxide tooth ceramic in contrast to their low tensile strength have a very high compressive strength, the occurrence of spalling is avoided even with thin geometries on the workpiece. Therefore, not only dental prostheses can be manufactured in a free-form milling process, which are significantly more delicate, with increased process stability now, but also the lifetime of the tools rises sharply, since now a change is needed only in the case of real forming of a wear on the tool, and not, as at present, it must be assumed, that the ruptures on the workpiece are due to a wear of the tool, although these ruptures inherently occur also with a tool which is not worn. At the same time the problem of chip stuck occurs never arise because of the pulverulent or dusty machining. After milling, due to the high milling accuracy, the dental prosthesis white body can be fully-sintered directly into the finished dental prosthesis, that is without need to be reworked.

With the ball end geometry, the point or area of engagement may migrate across the entire hemisphere at the free end of the dental milling tool, with widths of engagement in the ball end portion from 0.1 to 0.8 times the largest outer or outside diameter of the dental milling tool have been found best practice. It is therefore advantageous not to carry out a full cut, but merely a partial cut with 0.1 to 0.8 times the largest outer diameter as width of application (width of engagement), wherein the application area (area of engagement), i.e. the area in which the cutting edges stay in the material, can migrate over the entire hemisphere stricken by the ball end portion and over the adjoining cylinder stricken by axial cutting portion.

For the length of the sharp cutting edges, values of 0.5 to 1.5 times the largest outer diameter have been proved to be sufficient, as a higher depth of cut is rarely to be expected in a layer-wise removal in 3D-form milling processing.

To meet the demands on the manufacturing accuracy on the one hand and on the tool strength during milling machining of ceramic white bodies on the other hand, values of about 1-4 mm, preferably 2 to 3 mm for the largest outer diameter of the ball end portion and therewith at the same time for the constant outer diameter of the axial cutting portion adjoining the ball end portion have been proven to be suitable, in particular if the entire dental milling tool is master formed integrally from one material such as a hard metal, that has no predetermined breaking points in the form of solder joints. When milling dental prosthesis white bodies then no more additional finishing is necessary.

Particular preferably at each of the cutting edges a clearance (or clearance cut or free cut) is provided, preferably of 0.1 mm width or less and particularly preferably with a clearance angle of 12° to 25°. This allows that the entire maximum cutting length can be used for machining fine details on the zirconium oxide white body, wherein the maximum cutting length is preferably less than 0.5 to 1.5 times the largest outer diameter, so as to form a highly accurate copy of the CAD/CAM-data on the dental prosthesis white body with best surface quality and thus without finishing.

In order to give the cutting force in the outlined application case the right direction and size, suitable values for the rake angle (or cutting angle or chip angle) are 8° to 25°. It is in view of the pulverulent or dust-like chipping of the white pre-sintered ceramic material sufficient for the depth of the flutes and with respect to the tool strength advantageous, if a web diameter in the axial cutting portion is about 40% to 65%, preferably 50%-65% or even 55%-65% of the largest outer or external diameter. That is, when the round tool web portion which is out of reach of the flutes has an outer circumference with a diameter of approximately 40% to 65%, preferably 50%-65% or even 55%-65% of the outer circumference of the tool in the axial cutting portion and at the transition into the ball end portion. Thereby, the dental milling tool gains stiffness, while due to the pulverulent chipping or machining of the pre-sintered ceramic material a sufficient "chip removal" or material removal is achieved despite the shallow depth of the flute.

As regards the design of the flutes in terms of a high tool rigidity and the limited needs for chipping volume due to the pulverulent chipping of pre-sintered ceramic material, it is advantageous, particularly for a dental milling tool designed as a double-edged or double flute tool, if at least in the axial cutting portion the backward transition from the outer diameter at the cutting edge into the web diameter in the flute is via a transition region, which may in particular be formed in an arc segment shape. Therein, the outer diameter being displaced 90° in the circumferential direction as against the largest outer diameter on the cutting edges is at the transition region 65-85%, in particular approximately 75% of the largest outer diameter such that the tool is additionally stiffened. With such tools, revolution speeds of up to 50,000 r.p.m. are possible in free-form milling of zirconium oxide dental ceramics.

Furthermore, it has been found that it may be advantageous for certain applications if the dental milling tool has a small transverse cutting edge or dead center. As thereby immersion into the material is facilitated and the pressure during immersion is degraded somewhat. This is particularly evident at very deep infeeds in Z-direction (Z-deliveries). Without transverse cutting edge, in tests zirconium dust sedimented in the center near the tool tip and caused poorer surfaces. By suitable CAM-strategies (e.g. "circular immersion or dipping") however, this problem can also be avoided as well as by providing a transverse cutting edge on the dental milling tool.

BRIEF DESCRIPTION OF THE DRAWINGS

Further advantageous further developments of the invention are explained with reference to the accompanying drawings, which show an advantageous embodiment of the invention.

DETAILED DISCUSSION IN CONJUNCTION WITH THE DRAWINGS

Figure 1:
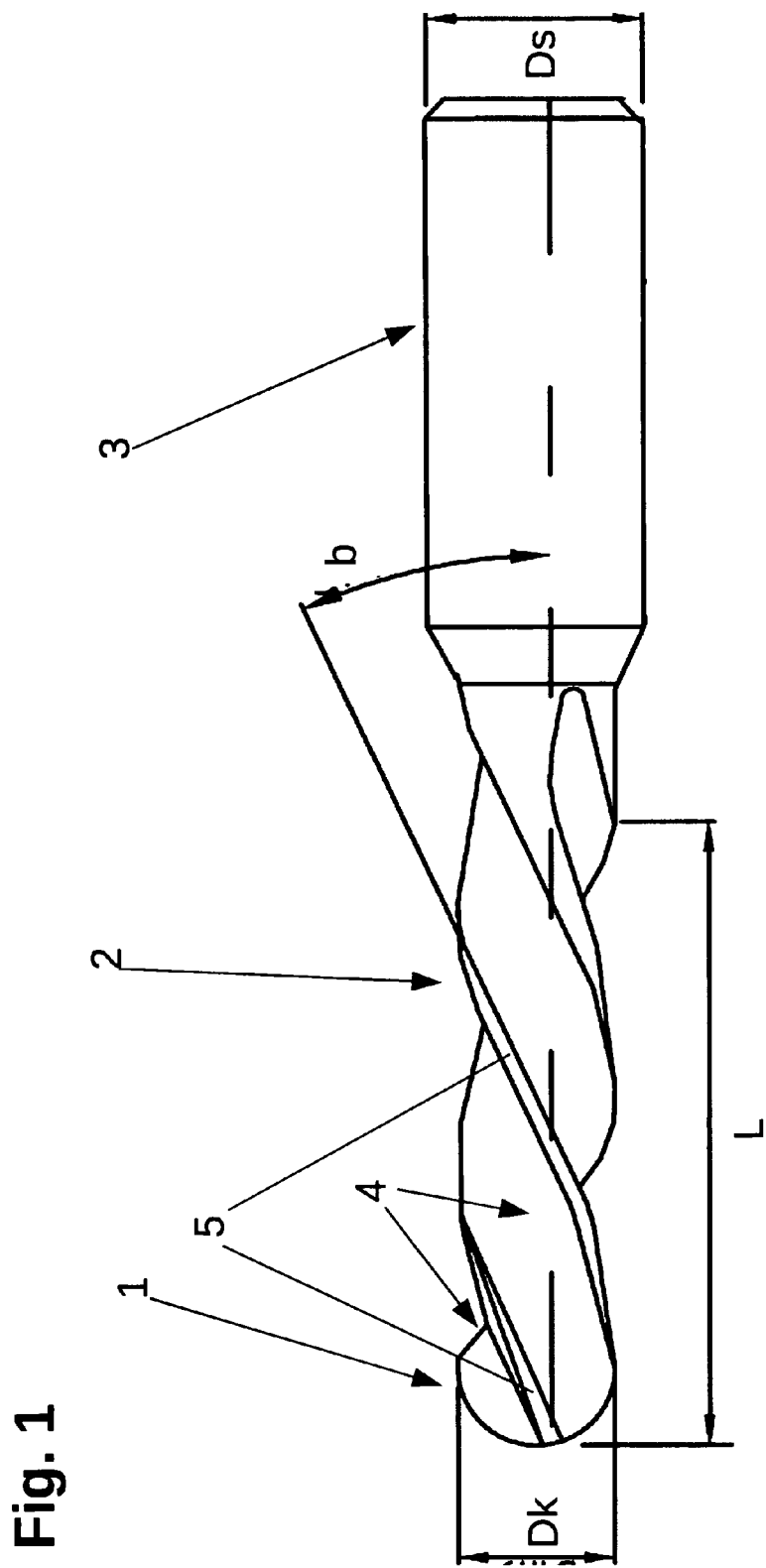
FIG. 1 shows a side view of a dental milling tool used according to an advantageous embodiment of the invention.

The dental milling tool shown in the figures has a ball end portion 1, an axial cutting portion 2 and a shank portion 3. The shank portion 3 has a diameter Ds which is greater than a constant outer diameter Dk in the axial cutting portion 2, that is a diameter Dk of the outer circumference of the dental cutter in the axial cutting portion 2. The ball end portion 1 of the dental mill is rounded hemispherical and transitions, with its largest outer diameter, which also corresponds to the diameter Dk of axial cutting portion 2, into the axial cutting portion 2.

Starting from the free end of the dental mill on the hemispherical rounded ball end portion 1, the dental milling tool comprises along its axial cutting portion 2 two flutes 4 extending spirally or helically coiled or twisted and two cutting teeth 5 separated from each other by the flutes, which are left-hand twisted, i.e. contrary to the clockwise direction of rotation provided for the dental cutter, with a twist angle b of 25° in the illustrated example. At the outer edges of the cutting teeth 5 facing in the clockwise direction of rotation the leading flute 4, cutting edges 6 extend. At the free end of the dental milling tool, the two cutting edges 6 are connected by a short transverse cutting edge or dead center 10.

If, within the scope of the present invention a hemispherical rounded ball end portion is mentioned, that means that the rounding there runs along the cutting edges 6 of the dental milling tool (double-edged in the example shown), or in other words, that the dental milling tool in side view and with a suitable radial positioning of the two edges has an approximately semi-circular contour in the ball end portion. Therein, the cutting edges 6, which extend in the transverse direction at the free end of the dental milling tool, lead into the cutting edge portions spiraled around the axial direction with a radius of approx. half the outer diameter Dk of the dental mill in the axial cutting portion 20.

This ensures that the dental milling tool can be used at any desired angle to the workpiece with an area of application migrating over the ball end portion 1. Therein, the sharp cutting edges 6 extend over an area of the axial cutting portion which is smaller than length L drawn in FIG. 1, which length L represents the length of the flutes plus the runout extending up to the transition to the shank portion 3.

Figure 2:
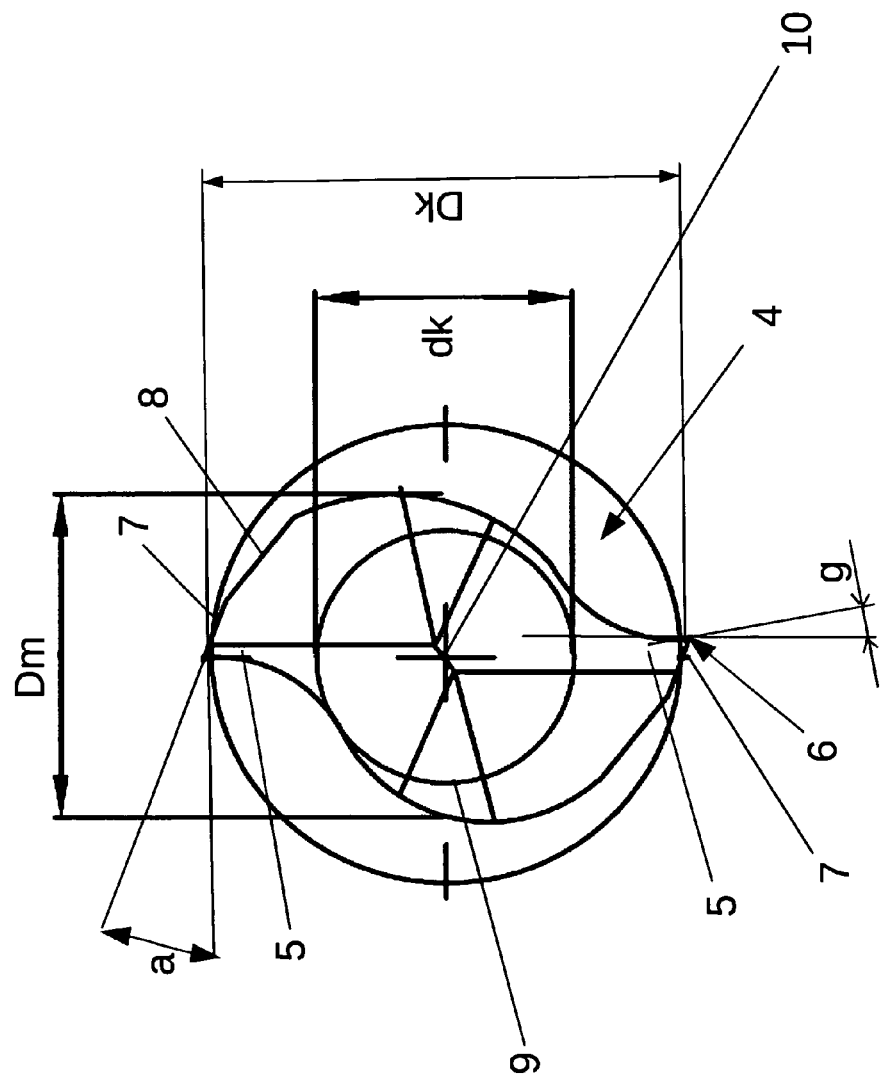
FIG. 2 shows an end view of the dental mill shown in FIG. 1 in enlarged view and omitting the cutter shank.

The sharp edges 6 extend, in the example shown, over a length equal to three times the largest outer diameter Dk of the ball end portion 1, which is the diameter Dk of the outer circumference of the axial cutting portion 2, so that it can be milled over a relatively large length on the coiled portions of the cutting edges 6 extending with the left-hand twist of the chip flutes 4. It is, as can be seen in FIG. 2, provided on the back of the cutting edge 6 a clearance 7, in the example shown with a clearance angle a of 20°. Through the clearance 7, also over a relatively large length of the sharp edges 6, a high surface quality is ensured on the ceramic white body to be machined, wherein a clearance surface 8 backwardly adjoining the clearance 7 and a arc segment shaped outwardly bulged transition region, which forms the transition into the respective flute and which in turn adjoins the clearance surface 8, has proven to be advantageous for low vibration and high rigidity of the tool.

Indeed, the space in the flutes available as chip volume is a bit small. Since the pre-sintered ceramic material to be worked, in particular zirconia is pulverulently machines, this can be tolerated in favor of rigidity of the above-mentioned tool. Also the maximum depth of the flutes 4 is relatively small, if one compares a web diameter dk of a milling tool web portion 9 (i.e. the diameter of the dental milling tool at the lowest point of the flutes 4) with the outer diameter Dk in the axial cutting portion. Here, this ratio in the example illustrated is approx. 55%. This, too, abets the life time of the dental milling tool. It should be noted that the inner circle is only drwan in FIG. 2 for illustrating the web diameter dk and dos not represent a physically existing feature.

For the desired purpose of machining zirconium oxide white bodies in the dental field, a two-edged design of the dental milling tool has proved to be advantageous in the sense of lower vibrations, although three-edged variants are also conceivable.

By left-hand twist of the flutes 4 and the cutting edges 6 at the cutting teeth 5 a tensile stress of the machined ceramic white body is avoided, thereby not only significantly better surface quality can be achieved, but also higher material removal or chip volume per unit time can be achieved, as compared with right twisted drills usual in the dental field.

The figures are not to scale. Thus, the end mill illustrated has an outer diameter Dk in the axial cutting portion 2 or at the end of the ball end portion 1 of 2 mm. For the purpose of 3D free-form milling of white sintered zirconium oxide ceramics, values from 1 to 4 mm, preferably 2 to 3 mm, for example 2 mm proved advantageous for the outside diameter Dk, in order to achieve the surface quality and dimensional accuracy required for dental prostheses such as dental implants, bridges or similar and at the same time high chip volume per unit time.

With the tool shown, all work steps can be carried out, i.e. after the layerwise removal of material by dental milling tool placed from above onto the ceramic white body, no additional finishing is needed anymore. That is, the dental prosthesis can be produced without tool change and thus with low production time, wherein in particular the left-hand twist and the corresponding lack of tensile loading lead to a low tendency for flaking and thus to a high surface quality. With the ball end portion 1 having the arcuate extending portions of the cutting edges, even the production of undercuts on the to be produced dental prosthesis is possible, if the end mill is used in a corresponding, for example, five-axis CNC milling machine, which allows an inclination of the dental milling tool relative to the workpiece during the machining operation.

Due to the pulverulent machining of ceramic white bodies, for which the dental milling tool is made, the flutes 4 even do not clog despite the left-hand twist, if driving into the solid material from above is carried out, without doing a chip removal in downwards direction is possible.

Variations and modifications of the embodiment shown are possible without departing from the core of the invention.

So it would be conceivable, for example, to select the diameter Ds of the shank portion 3 equal to the largest outside diameter Dk of the ball end portion 1 and thus to produce an end mill with the same outer diameter almost throughout its entire length. Smaller, however, the diameter should not be chosen so as not to endanger the stability of the tool. While with the twist angle b of 25° and also in the range of 5° to 30° around this value particularly good results have been obtained in experiments at zirconium oxide round blanks, it is possible to vary this twist angle within wide limits, as long as it remains at a left-hand twist and the right cutting direction of the dental mill and thus at a pressure load on the to be processed, pre-sintered ceramic round blank during immersion of the dental milling tool into the solid material from above.

The invention claimed is:

1. Milling method for the manufacture of dental prostheses, wherein, on a multi-axis CNC-milling machine, with a dental milling tool for milling dental prostheses white bodies out of pre-sintered raw white bodies, which dental prostheses white bodies afterwards have to be fully-sintered into dental prostheses, using 3D free-form milling along generated travel paths, a dental prosthesis white body is milled out of a pre-sintered ceramic white body, especially a pre-sintered zirconium oxide white body, wherein the ceramic white body is provided in the form of a plate or a round blank, and wherein the dental milling tool is driven from above into the solid material of the ceramic white body and, prior to this, the ceramic white body is clamped, and, subsequently, by layer-wise removal of material along the generated paths, the dental prosthesis white body is milled out of the ceramic white body, characterized in that the dental milling tool comprises a hemispherical rounded ball end portion (1), which, with its largest outside diameter (Dk) of about 1-4 mm or 2-3 mm, goes over into an axial cutting portion (2) axially extending constantly with this diameter (Dk) on its outer circumference, wherein a shank portion (3) adjoins to the axial cutting portion (2) having a larger or at least equally large shank diameter (Ds), wherein the dental milling tool further comprises two chip flutes (4) and a corresponding number of cutting teeth (5), which, from the ball-head portion (1) along the axial cutting portion (2), are coiled around a web portion (9) consisting of solid material and having a circular cross-section, and wherein, at such outer edge of each cutting tooth (5) facing the flute (4) in direction of clockwise rotation, a cutting edge (6) is provided, being in the ball end portion (1) arcuate, seen in axial direction, and being in the axial cutting portion (2) on the radial coordinate of the maximum outside diameter (Dk), and wherein all the flutes (4) and the cutting teeth (5) are coiled with a left-hand twist, the twist angle (b) is 1°-45°, in particular 5° to 30°.

2. Milling method according to claim 1, characterized in that the dental prosthesis white body, which afterwards has to be fully-sintered to the finished dental prosthesis, is milled out with a single dental milling tool.

3. Milling method according to claim 2, characterized in that the milled dental prosthesis white body is subsequently fully-sintered into the finished dental prosthesis.

4. Milling method according to claim 1, characterized in that the ball end portion (1), the axial cutting portion (2) and the shank portion (3) of the dental milling tool are integrally master formed of one material.

5. Milling method according to claim 4, characterized in that at each of the cutting edges (6) of the dental milling tool a clearance (7) is provided.

6. Milling method according to claim 5, characterized in that the width of each of the clearances (7) is 0.1 mm or less.

7. Milling method according to claim 6, characterized in that each of the clearances (7) has a clearance angle of 12°-25°.

8. Milling method according to claim 7, characterized in that on each of the cutting edges (6), at least in the axial cutting portion (2) of the dental milling tool, a rake angle of 8° to 25° is provided.

9. Milling method according to claim 7, characterized in that a transition of each cutting edge (6) of the dental milling tool into a corresponding flute (4) in direction against the clockwise direction of rotation is via a clearance surface directly adjoining on the backside or via a clearance surface (8) adjoining on the backside of the clearance (7).

10. Milling method according to claim 9, characterized in that the dental milling tool is formed as a double flute mill and, in the axial cutting portion (2), the backward transition from the outer diameter (Dk) of the cutting edge (6) to the web diameter (dk) in the flute (4) is via a particular arc segment-shaped transition region, which adjoins clearance surface (8), wherein an outer diameter (Dm) being displaced 90° in the circumferential direction as against the largest outer diameter (Dk) on the cutting edges (6) is at the transition region 65-85% of the largest outer diameter (Dk).

11. Milling method according to claim 10, characterized in that the largest outer diameter (Dk) on the cutting edges (6) is at the transition region approximately 75% of the largest outer diameter (Dk).

12. Milling method according to claim 9, characterized in that the cutting edges (6) of the dental milling tool have a length (L), which equates in the axial direction at least 50% to 150% of the largest outer diameter (Dk) of the largest outer diameter (Dk).

13. Milling method according to claim 9, characterized in that the length (L), of the cutting edges (6) of the dental milling tool equates in the axial direction 100% to 150% of the largest outer diameter (Dk).

14. Milling method according to claim 4, characterized in that the web portion of the dental milling tool has an outer circumference with a diameter of about 40 to 65% of a diameter of the outer circumference of the tool in the axial cutting portion and at the transition into the ball end portion.

15. Milling method according to claim 14, characterized in that the diameter of the web portion of the dental milling tool is 50%-65% of a diameter of the outer circumference of the tool in the axial cutting portion and at the transition into the ball end portion.

16. Milling method according to claim 15, characterized in that the diameter of the web portion of the dental milling tool is 55%-65% of a diameter of the outer circumference of the tool in the axial cutting portion and at the transition into the ball end portion.

17. Milling method according to claim 4, characterized in that at least in the region of the ball end portion of the dental milling tool a wear protection coating is provided, in particular a coating of hard material, including diamond or cubic boron nitride.

18. Milling method according to claim 14, characterized in that the one material is a hard metal.

* * * * *